US009121832B2

(12) United States Patent
Beselt et al.

(10) Patent No.: US 9,121,832 B2
(45) Date of Patent: Sep. 1, 2015

(54) APPARATUS AND METHOD FOR REDUCING VIBRATIONS OF SCANNING SENSORS IN WEB MANUFACTURING OR PROCESSING SYSTEMS

(75) Inventors: Ronald E. Beselt, Burnaby (CA); Salvatore Chirico, Port Moody (CA); Gary K. Burma, West Vancouver (CA); Michael J. Wardas, North Vancouver (CA)

(73) Assignee: Honeywell ASCa Inc., Ontario (CA)

( * ) Notice: Subject to any disclaimer, the term of this patent is extended or adjusted under 35 U.S.C. 154(b) by 1035 days.

(21) Appl. No.: 13/223,566

(22) Filed: Sep. 1, 2011

(65) Prior Publication Data

US 2013/0055912 A1 Mar. 7, 2013

(51) Int. Cl.
*B41L 23/02* (2006.01)
*G01N 21/89* (2006.01)

(52) U.S. Cl.
CPC .................................. *G01N 21/8901* (2013.01)

(58) Field of Classification Search
USPC ........................................ 73/159, 430, 11.09
See application file for complete search history.

(56) References Cited

U.S. PATENT DOCUMENTS

| 4,271,699 A * | 6/1981 | Williamson ..................... 73/159 |
| 2004/0165923 A1* | 8/2004 | Karin et al. .................... 400/323 |
| 2006/0111808 A1* | 5/2006 | Burma .......................... 700/129 |
| 2009/0099682 A1* | 4/2009 | Jasinski ........................ 700/128 |
| 2009/0122284 A1* | 5/2009 | Butler et al. .................... 355/53 |
| 2011/0141181 A1* | 6/2011 | Ito et al. ......................... 347/16 |

OTHER PUBLICATIONS

Tuned mass damper of Purdue University (See attachment).*
Thomas H. Steele, "Experion MX—Quality Control System Delivers Lowest Total Cost of Ownership", Honeywell Process Solutions, Sep. 2010, 8 pages.
"Experion MX O-Frame Scanner", Product Information Note, Honeywell, Nov. 2010, 5 pages.
Wikipedia, "Tuned Mass Damper", http://en.wikipedia.org/wiki/Tuned_mass_damper, Aug. 2011, 7 pages.

* cited by examiner

*Primary Examiner* — Hezron E Williams
*Assistant Examiner* — Xin Zhong

(57) ABSTRACT

An apparatus includes a scanning head configured to move one or more sensors back and forth across a surface of a moving web of material. The apparatus also includes a vibration dampening device configured to reduce vibrations of the one or more sensors when the scanning head moves the one or more sensors back and forth across the surface of the web. The vibration dampening device includes at least one mass and one or more springs configured to create oscillatory movement of the at least one mass. The at least one mass and the one or more springs can be located within a housing that rides on a rail back and forth to move the scanning head across the surface of the web. The at least one mass and the one or more springs can also be located on a web deflector connected to the scanning head.

20 Claims, 6 Drawing Sheets

APPARATUS AND METHOD FOR REDUCING VIBRATIONS OF SCANNING SENSORS IN WEB MANUFACTURING OR PROCESSING SYSTEMS

TECHNICAL FIELD

This disclosure relates generally to web manufacturing or processing systems. More specifically, this disclosure relates to an apparatus and method for reducing vibrations of scanning sensors in web manufacturing or processing systems.

BACKGROUND

Sheets or other webs of material are often used in a variety of industries and in a variety of ways. These materials can include paper, multi-layer paperboard, and other products manufactured or processed in long webs. As a particular example, long sheets of paper can be manufactured and collected in reels.

Often times, a web needs to be manufactured or processed to have certain specified characteristics, such as a specific color or basis weight. In many web manufacturing or processing systems, scanners are used to capture sensor measurements of various characteristics of a web. The sensor measurements are provided to a controller, which uses the sensor measurements to adjust the manufacturing or processing system. Ideally, the controller operates to ensure that the characteristics of the web remain at or near desired values.

Accurate sensor measurements are typically needed in order to properly control a web manufacturing or processing system. Inaccurate sensor measurements can lead to improper control of the system, resulting in a finished product that fails to meet necessary specifications.

SUMMARY

This disclosure provides an apparatus and method for reducing vibrations of scanning sensors in web manufacturing or processing systems.

In a first embodiment, an apparatus includes a scanning head configured to move one or more sensors back and forth across a surface of a moving web of material. The apparatus also includes a vibration dampening device configured to reduce vibrations of the one or more sensors when the scanning head moves the one or more sensors back and forth across the surface of the web. The vibration dampening device includes at least one mass and one or more springs configured to create oscillatory movement of the at least one mass.

In a second embodiment, an apparatus includes a scanning head configured to move back and forth across a surface of a moving web of material. The apparatus also includes a sheet deflector connected to the scanning head and configured to deflect the web. In addition, the apparatus includes a vibration dampening device connected to the sheet deflector and configured to reduce vibrations of the scanning head. The vibration dampening device includes at least one mass and one or more springs configured to create oscillatory movement of the at least one mass.

In a third embodiment, a method includes moving a scanning head back and forth across a surface of a moving web of material. The scanning head includes one or more sensors measuring at least one characteristic of the web. The method also includes reducing vibrations of the one or more sensors when the scanning head moves the one or more sensors back and forth across the surface of the web using a vibration dampening device. The vibration dampening device includes at least one mass and one or more springs that create oscillatory movement of the at least one mass.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 5, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
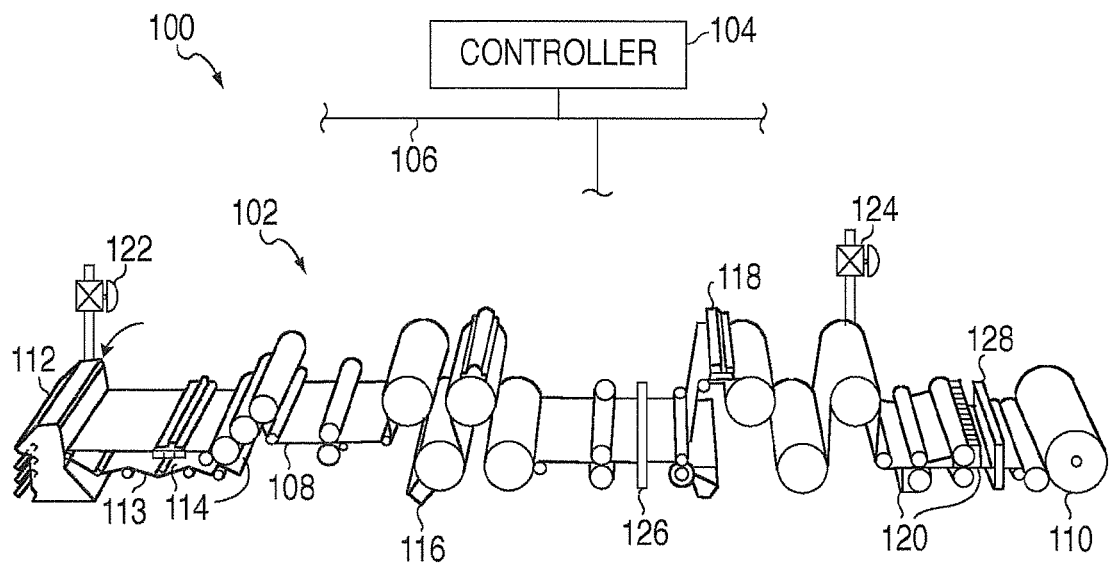
FIG. 1 illustrates an example web manufacturing or processing system according to this disclosure.

FIG. 1 illustrates an example web manufacturing or processing system 100 according to this disclosure. In this example, the system 100 includes a paper machine 102, a controller 104, and a network 106. The paper machine 102 includes various components used to produce a paper product, namely a paper web 108 collected at a reel 110. The controller 104 monitors and controls the operation of the paper machine 102, which may help to maintain or increase the quality of the paper web 108 produced by the paper machine 102.

In this example, the paper machine 102 includes at least one headbox 112, which distributes a pulp suspension uniformly across the machine onto a continuous moving wire screen or mesh 113. The pulp suspension entering the headbox 112 may contain, for example, 0.2-3% wood fibers, fillers, and/or other materials, with the remainder of the suspension being water. The headbox 112 may include an array of dilution actuators, which distributes dilution water into the pulp suspension across the web. The dilution water may be used to help ensure that the resulting paper web 108 has a more uniform basis weight across the web 108.

Arrays of drainage elements 114, such as vacuum boxes, remove as much water as possible. An array of steam actuators 116 produces hot steam that penetrates the paper web 108 and releases the latent heat of the steam into the paper web 108, thereby increasing the temperature of the paper web 108 in sections across the web. The increase in temperature may allow for easier removal of remaining water from the paper web 108. An array of rewet shower actuators 118 adds small droplets of water (which may be air atomized) onto the surface of the paper web 108. The array of rewet shower actuators 118 may be used to control the moisture profile of the paper web 108, reduce or prevent over-drying of the paper web 108, or correct any dry streaks in the paper web 108.

The paper web 108 is then often passed through a calender having several nips of counter-rotating rolls. Arrays of induction heating actuators 120 heat the shell surfaces of various ones of these rolls. As each roll surface locally heats up, the roll diameter is locally expanded and hence increases nip pressure, which in turn locally compresses the paper web 108. The arrays of induction heating actuators 120 may therefore be used to control the caliper (thickness) profile of the paper web 108. The nips of a calender may also be equipped with other actuator arrays, such as arrays of air showers or steam showers, which may be used to control the gloss profile or smoothness profile of the paper web.

Two additional actuators 122-124 are shown in FIG. 1. A thick stock flow actuator 122 controls the consistency of incoming stock received at the headbox 112. A steam flow actuator 124 controls the amount of heat transferred to the paper web 108 from drying cylinders. The actuators 122-124 could, for example, represent valves controlling the flow of stock and steam, respectively. These actuators may be used for controlling the dry weight and moisture of the paper web 108.

Additional components could be used to further process the paper web 108, such as a supercalender (for improving the paper web's thickness, smoothness, and gloss) or one or more coating stations (each applying a layer of coatant to a surface of the paper to improve the smoothness and printability of the paper web). Similarly, additional flow actuators may be used to control the proportions of different types of pulp and filler material in the thick stock and to control the amounts of various additives (such as retention aid or dyes) that are mixed into the stock.

This represents a brief description of one type of paper machine 102 that may be used to produce a paper product. Additional details regarding this type of paper machine 102 are well-known in the art and are not needed for an understanding of this disclosure. Also, this represents one specific type of paper machine 102 that may be used in the system 100. Other machines or devices could be used that include any other or additional components for producing a paper product. In addition, this disclosure is not limited to use with systems for producing paper products and could be used with systems that process a paper product or with systems that produce or process other items or materials (such as multi-layer paperboard, cardboard, plastic, textiles, metal foil or webs, or other or additional materials that are manufactured or processed as moving webs).

In order to control the paper-making process, one or more properties of the paper web 108 may be continuously or repeatedly measured. The web properties can be measured at one or various stages in the manufacturing process. This information may then be used to adjust the paper machine 102, such as by adjusting various actuators within the paper machine 102. This may help to compensate for any variations of the web properties from desired targets, which may help to ensure the quality of the web 108.

As shown in FIG. 1, the paper machine 102 includes one or more scanners 126-128, each of which may include one or more sensors. Each scanner 126-128 is capable of scanning the paper web 108 and measuring one or more characteristics of the paper web 108. For example, each scanner 126-128 could include sensors for measuring the anisotropy, color, gloss, sheen, haze, surface features (such as roughness, topography, or orientation distributions of surface features), or any other or additional characteristics of the paper web 108.

Each scanner 126-128 includes any suitable structure or structures for measuring or detecting one or more characteristics of the paper web 108, such as sets or arrays of sensors. The use of multiple scanning sets of sensors represents one particular embodiment for measuring web properties. Other embodiments could be used, such as those including one or more stationary sets or arrays of sensors, deployed in one or a few locations across the web or deployed in a plurality of locations across the whole width of the web such that substantially the entire web width is measured. However, the system 100 generally includes at least one scanning set of sensors at one or more locations.

The controller 104 receives measurement data from the scanners 126-128 and uses the data to control the paper machine 102. For example, the controller 104 may use the measurement data to adjust any of the actuators or other components of the paper machine 102. The controller 104 includes any suitable structure for controlling the operation of at least part of the paper machine 102, such as a computing device.

The network 106 is coupled to the controller 104 and various components of the paper machine 102 (such as the actuators and scanners). The network 106 facilitates communication between components of system 100. The network 106 represents any suitable network or combination of networks facilitating communication between components in the system 100. The network 106 could, for example, represent a wired or wireless Ethernet network, an electrical signal network (such as a HART or FOUNDATION FIELDBUS network), a pneumatic control signal network, or any other or additional network(s).

As noted above, accurate sensor measurements from the scanners 126-128 are often needed in order to ensure effective control of the paper machine 102 by the controller 104. However, scanning sensors often vibrate during movement across the web 108. Vibrations that occur during sensor measurements may be sufficient to negatively impact the scanner's performance. For example, the vibrations could cause the scanner 126-128 to generate inaccurate or incorrect sensor measurements. As described below, at least one scanner 126-128 includes a mechanism for reducing vibrations of a scanning head, which contains one or more sensors. This can help to increate the accuracy and reliability of the sensors' measurements, leading to improved control of the paper machine 102.

Although FIG. 1 illustrates one example of a web manufacturing or processing system 100, various changes may be made to FIG. 1. For example, other systems could be used to produce paper products or other products. Also, while shown as including a single paper machine 102 with various components and a single controller 104, the production system 100 could include any number of paper machines or other production machinery having any suitable structure, and the system 100 could include any number of controllers. In addition, FIG. 1 illustrates one operational environment in which vibration reduction for a web scanner can be used. This functionality could be used in any other suitable system.

Figure 2B:
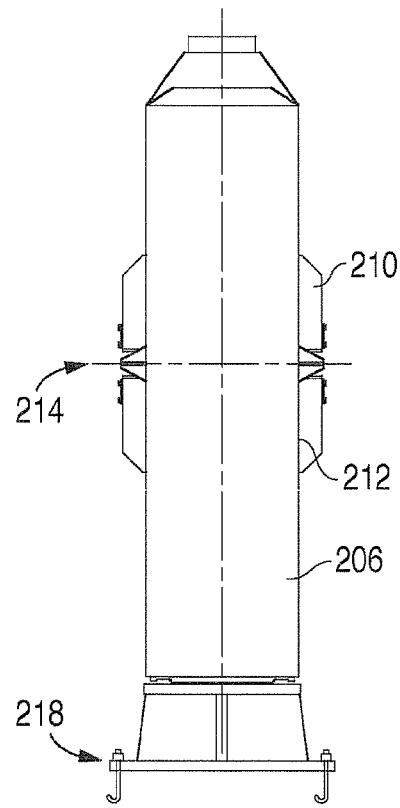
FIGS. 2A and 2B illustrate an example scanner in a web manufacturing or processing system according to this disclosure.
Figure 2A:
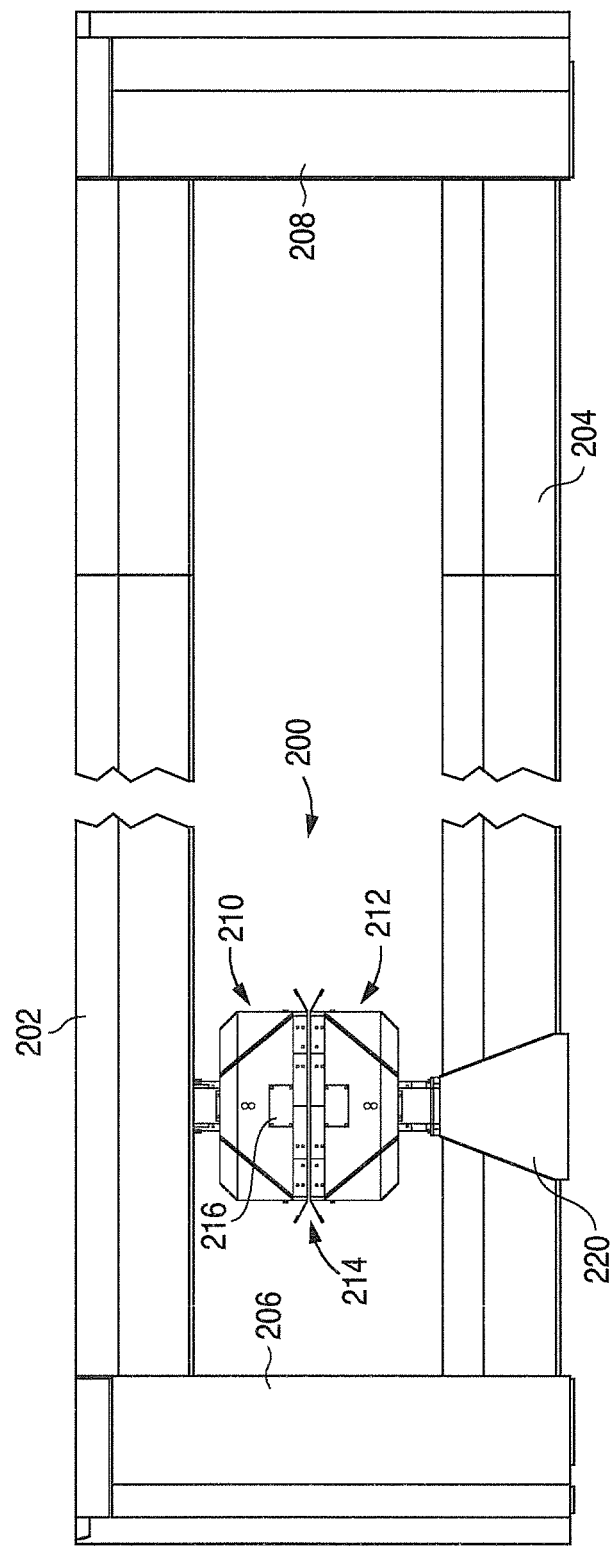

FIGS. 2A and 2B illustrate an example scanner 200 in a web manufacturing or processing system according to this disclosure. The scanner 200 could, for example, be used as the scanner(s) 126 or 128 in the system 100 of FIG. 1. As shown in FIG. 2A, the scanner 200 runs across upper and lower rails 202-204, and support structures 206-208 maintain separation of the rails 202-204. The web 108 passes generally horizontally between the support structures 206-208, and the rails 202-204 allow sensors in the scanner 200 to pass over at least one surface of the web 108 as the scanner 200 moves left and right in FIG. 2A.

In this example, the scanner 200 includes upper and lower scanning heads 210-212. The scanning heads 210-212 denote structures that pass over upper and lower surfaces of the web 108 as the web 108 passes through a gap 214 between the scanning heads 210-212.

One or more sensors 216 in one or both scanning heads 210-212 capture sensor measurements of the web 108. The actual sensing operations can vary depending on the type(s) of sensor measurements being taken. For example, some types of sensor measurements can be taken by sensors 216 in both scanning heads 210-212. As a particular example, each scanning head 210-212 could generate and measure light reflected off the surface of the web 108. Other types of sensor measurements may be taken by a sensor 216 in only one scanning head, and the other scanning head could be used to support those sensor measurements. As a particular example, one scanning head could generate light that passes through the web 108, where a sensor 216 in the other scanning head measures the light coming from the web 108. Any suitable type(s) of sensor measurement(s) could be taken using the scanner 200.

Each rail 202-204 includes any suitable structure across which a scanner 200 can be moved. Also, any suitable drive mechanism can be used to move the scanner 200 across the rails 202-204, such as a drive belt. Each support structure 206-208 includes any suitable structure for maintaining separation of rails 202-204. Each scanning head 210-212 includes any suitable structure for moving components across a surface of a web 108. Each sensor 216 includes any suitable structure for measuring one or more characteristics of a web 108.

As shown in FIG. 2B, each support structure 206-208 includes a mounting device 218 that couples the support structure 206-208 to an external surface. The mounting device 218 includes any suitable device for connecting the support structure 206-208 to an external surface.

As can be seen in FIG. 2A, the lower scanning head 212 is mounted on a carriage 220. The carriage 220 moves back and forth across the lower rail 204 to move the lower scanning head 212 across a surface of the web 108. Moreover, the carriage 220 includes a vibration dampening device that helps to reduce vibrations experienced by any sensors 216 in the lower scanning head 212. The vibration dampening device includes a tuned spring/mass or spring/mass/damper structure. Additional details regarding the use of a tuned spring/mass or spring/mass/damper structure are provided below.

Although FIGS. 2A and 2B illustrate one example of a scanner 200 in a web manufacturing or processing system, various changes may be made to FIGS. 2A and 2B. For example, each structure in FIGS. 2A and 2B could have any suitable size, shape, and dimensions and be formed from any suitable material(s). Also, while a single pair of upper and lower scanning heads 210-212 are shown here, a scanner 200 could include multiple pairs of upper and lower scanning heads 210-212, where each pair is responsible for scanning a smaller portion of the web 108.

Figure 3A:
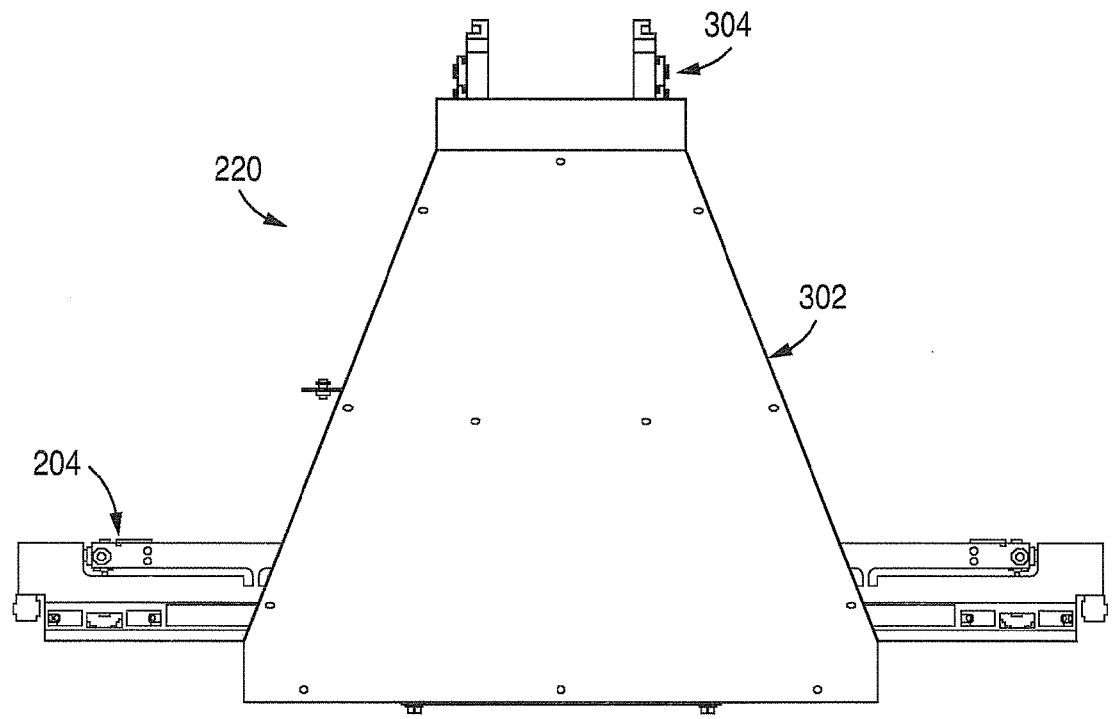
FIGS. 3A through 3C illustrate an example scanner carriage having a mechanism for reducing vibration in a web manufacturing or processing system according to this disclosure.
Figure 3B:
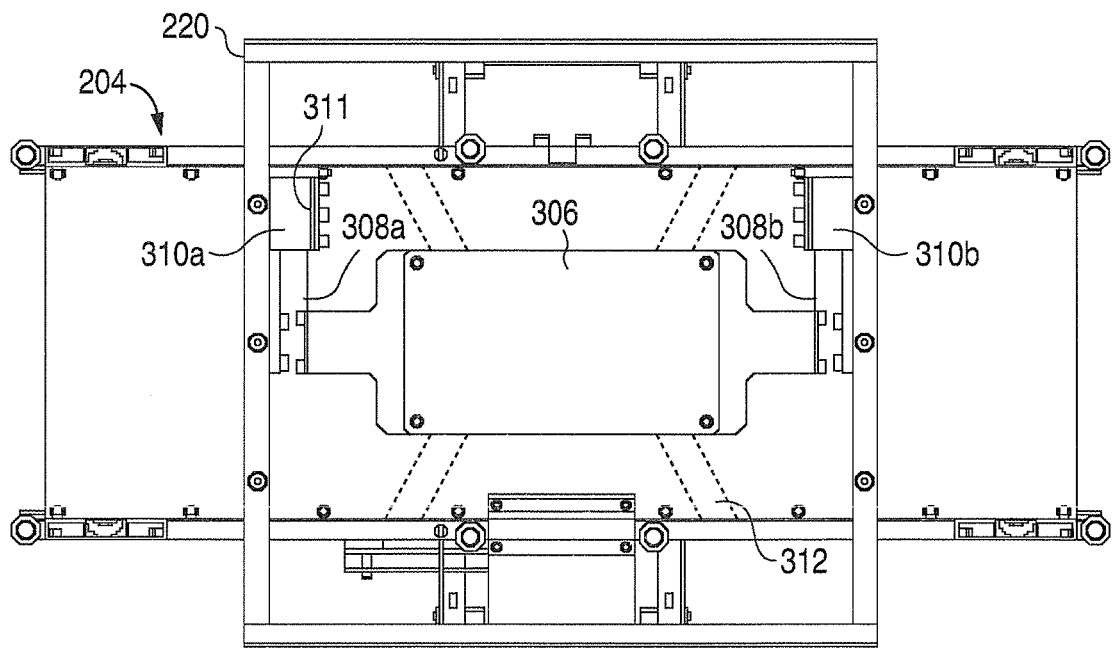
Figure 3C:
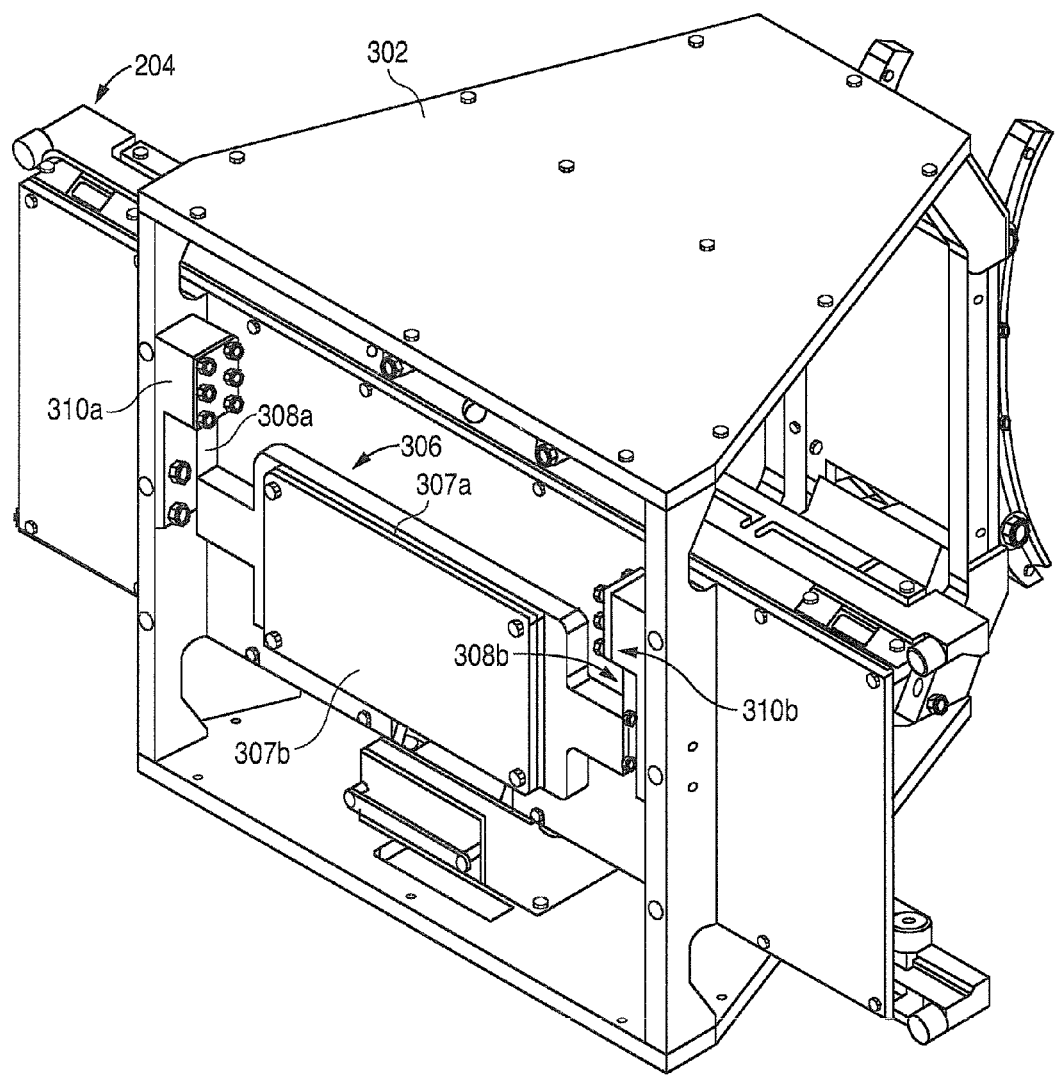

FIGS. 3A through 3C illustrate an example scanner carriage 220 having a mechanism for reducing vibration in a web manufacturing or processing system according to this disclosure. As shown in FIGS. 3A and 3B, the scanner carriage 220 includes a housing 302 and a scanning head mount 304. The housing 302 generally houses various components that allow the lower scanning head 212 to ride on the lower rail 204.

These components can include wheels and couplers attached to a drive belt. The housing 302 in this example has a trapezoidal shape, although the housing 302 could have any other suitable shape. The scanning head mount 304 couples the scanner carriage 220 to the lower scanning head 212. The scanning head mount 304 includes any suitable structure for connecting the scanner carriage 220 to the lower scanning head 212.

As shown in FIGS. 3B and 3C, the scanner carriage 220 includes a mechanism for reducing vibration experienced by the lower scanning head 212. The mechanism here represents a tuned spring/mass structure having a mass 306 and springs 308a-308b. The mass 306 generally represents any suitable structure having a desired mass. The springs 308a-308b generally represent any suitable structures for causing oscillatory movements of the mass 306. In this example, each spring 308a-308b represents a flexible sheet of metal or other material having a specified length, thickness, and width (which can vary from scanner to scanner). However, the springs 308a-308b could represent any other suitable structure(s), such as cantilevered strips of metal, helical metal or other types of springs, or elastomers. Also note that any number of springs could be used.

Two couplers 310a-310b couple the springs 308a-308b to the housing 302. In this example, each coupler 310a-310b includes a thicker section physically connected to one of the springs 308a-308b (such as by bolts or other connecting structures). Each coupler 310a-310b also includes a narrower section physically connected to the housing 302.

In this example, various features can be used to tune the spring/mass structure. For example, the mass 306 includes a base 307a and one or more plates 307b. The base 307a is connected to the springs 308a-308b and has some mass. Additional mass can be added to the structure by connecting one or more plates 307b to the base 307a. In this way, the mass of the spring/mass structure can be adjusted to provide a desired vibration reduction. In particular embodiments, the base 307a could represent a larger mass, while the plates 307b could have smaller masses that allow finer adjustment of the total mass. Also, one or more shims 311 could be inserted between the couplers 310a-310b and the springs 308a-308b, allowing the spring/mass structure to be used in housings 302 of different sizes.

Optionally, a damper 312 can be placed between the mass 306 and the housing 302. The damper 312 further reduces vibrations of the lower scanning head 212. The damper 312 generally represents any suitable structure for converting kinetic energy into heat, such as an elastomeric material or other material(s) or a dashpot. With the damper 312 present, this creates a spring/mass/damper structure within the housing 302. Note that the shape, size, and number of portions of damper 312 are for illustration only. The damper 312 could have any suitable size and shape, and damping material or other structures at any number of locations can be used in the scanner 200.

The spring/mass structure or the spring/mass/damper structure can be tuned for the specific implementation of the scanner head 212. For example, the mass of the mass 306 and the characteristics of the springs 308a-308b (such as length, thickness, or width) can be selected based on various factors, such as the mass of the scanning head 212 and the remainder of the carriage 220. In general, the physics of spring/mass and spring/mass/damper structures are well known and can be used to tune these structures for a specific scanning device.

In general, the spring/mass or spring/mass/damper structure operates by allowing the mass 306 to move in a direction opposite the direction of the scanning head's movement. That is, the mass 306 moves to the right when the scanning head 212 starts moving left, and the mass 306 moves to the left when the scanning head 212 starts moving right. When the lower scanning head 212 moves back and forth, this creates an oscillating motion of the mass 306. However, the mass 306 oscillates in the opposite direction compared to the scanning head 212. Ideally, the oscillating motion of the mass 306 helps to reduce vibrations in the lower scanning head 212 caused by the back and forth motion of the lower scanning head 212. As a result, one or more sensors 216 in the lower scanning head 212 can capture more accurate or reliable sensor measurements.

Note that in this example, the spring/mass or spring/mass/damper structure is used to reduce horizontal vibration experienced by the scanning head 212. Of course, other or additional spring/mass or spring/mass/damper structures could be used to reduce other or additional vibrations. For example, a second spring/mass or spring/mass/damper structure could be used to reduce vertical vibration experienced by the scanning head 212.

Although FIGS. 3A through 3C illustrate one example of a scanner carriage 220 having a mechanism for reducing vibration in a web manufacturing or processing system, various changes may be made to FIGS. 3A through 3C. For example, each structure in FIGS. 3A through 3C could have any suitable size, shape, and dimensions and be formed from any suitable material(s).

Note that the location of the spring/mass or spring/mass/damper structure at the bottom of the housing 302 is for illustration only. A spring/mass or spring/mass/damper structure could be placed at any other suitable location(s) that can help to reduce vibrations of the scanning head 212.

Figure 4A:
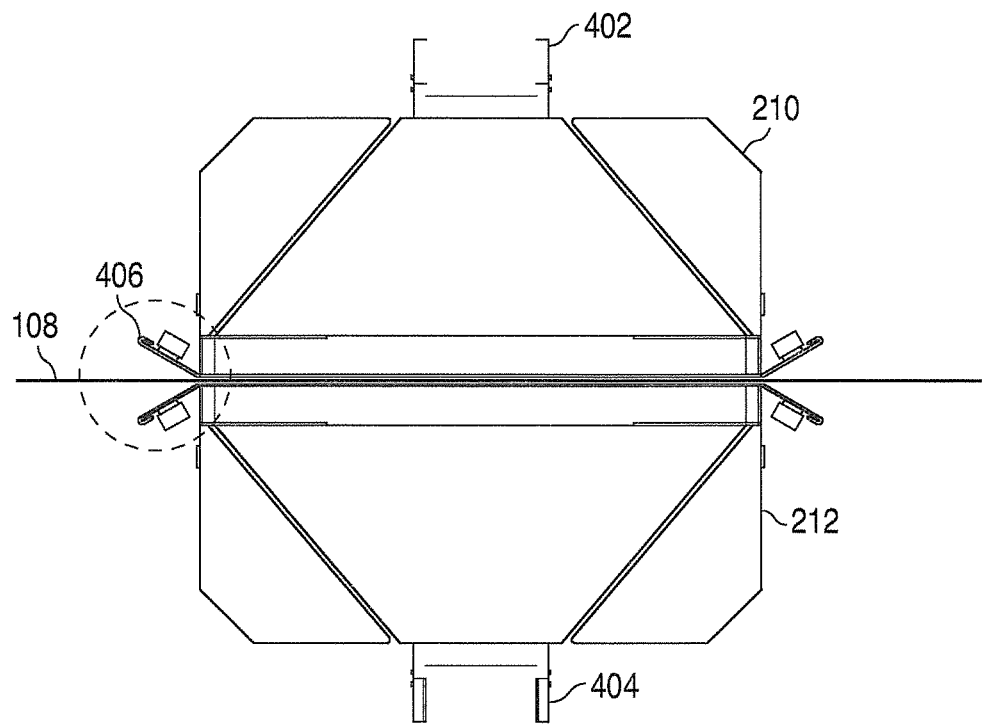
FIGS. 4A through 4C illustrate example web deflectors having a mechanism for reducing vibration in a web manufacturing or processing system according to this disclosure.
Figure 4B:
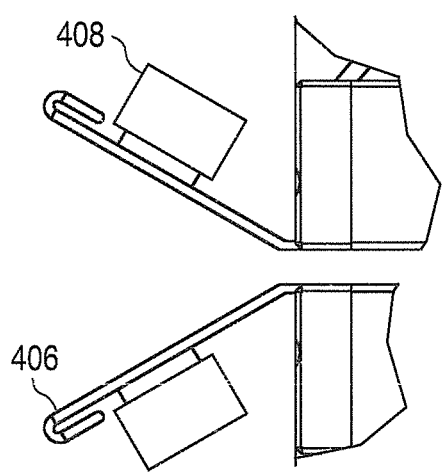
Figure 4C:
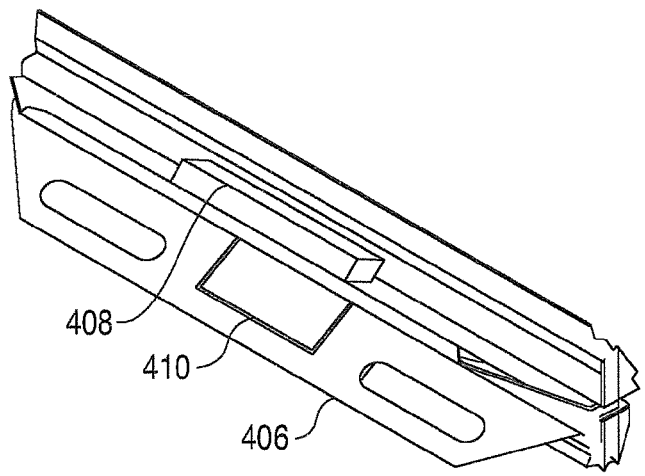

FIGS. 4A through 4C illustrate example web deflectors having a mechanism for reducing vibration in a web manufacturing or processing system according to this disclosure. FIG. 4A illustrates an enlarged portion of the scanner 200 of FIG. 2A with the upper and lower scanning heads 210-212. The upper scanning head 210 includes a mount 402 that can be connected to an upper carriage that rides on the upper rail 202. The lower scanning head 212 includes a mount 404 that can be connected to the carriage 220 using the mounting device 218.

As shown in FIG. 4A, two web deflectors 406 are connected to the upper scanning head 210, and two web deflectors 406 are connected to the lower scanning head 212. The circled portion of the scanner in FIG. 4A is shown in greater detail in FIG. 4B. The web deflectors 406 help to deflect the web 108 and guide the web 108 into the gap 214 between the scanning heads 210-212 to maintain the position of the web 108 within the gap 214. Each web deflector 406 includes any suitable structure for guiding a web 108, such as a cantilevered arm connected to a scanning head. Each web deflector 406 could be formed from any suitable material(s), such as a metal sheet.

As shown in FIGS. 4A through 4C, each web deflector 406 is connected to a tuned spring/mass structure, which includes a mass 408 and a spring 410. The mass 408 generally represents any suitable structure having a desired mass. The spring 410 generally represents any suitable structure for causing oscillatory movements of the mass 408. In this example, the spring 410 represents a portion of the web deflector 406 that has been cut on three sides to allow the mass 408 to move. Once again, the spring/mass structure can be tuned to reduce or eliminate a specific type of vibration. For instance, in some embodiments, the mass 408 could have the structure shown in FIG. 3C with the base 307a and optionally one or more plates 307b to achieve a desired total mass. The mass 408 and the dimensions of the spring 410 can be selected to achieve a desired tuning. Note, however, that the mass 408 and spring 410 could have any other suitable form.

The tuned spring/mass structure here effectively converts a single-purpose web deflector into a multi-purpose device. Now, the web deflector 406 can function to deflect the web 108 and to reduce vibrations. This functionality could be essentially transparent to an end user.

Although FIGS. 4A through 4C illustrate one example of web deflectors having a mechanism for reducing vibration in a web manufacturing or processing system, various changes may be made to FIG. 4A through 4C. For example, not all web deflectors 406 may be connected to a tuned spring/mass structure. One, two, three, or four web deflectors 406 may be connected to tuned spring/mass structures. Also, there may be more than one mass or spring on each web deflector 406. Further, the shape and orientation of the tuned mass/spring structures can vary. In addition, although not shown, a damper could also be used with one or more of the spring/mass structures.

Note that FIGS. 2A through 4C illustrate example locations where one or more tuned spring/mass or spring/mass/damper structures can be used in a web manufacturing or processing system. Other positions for the spring/mass or spring/mass/damper structure(s) could also be used.

Figure 5:
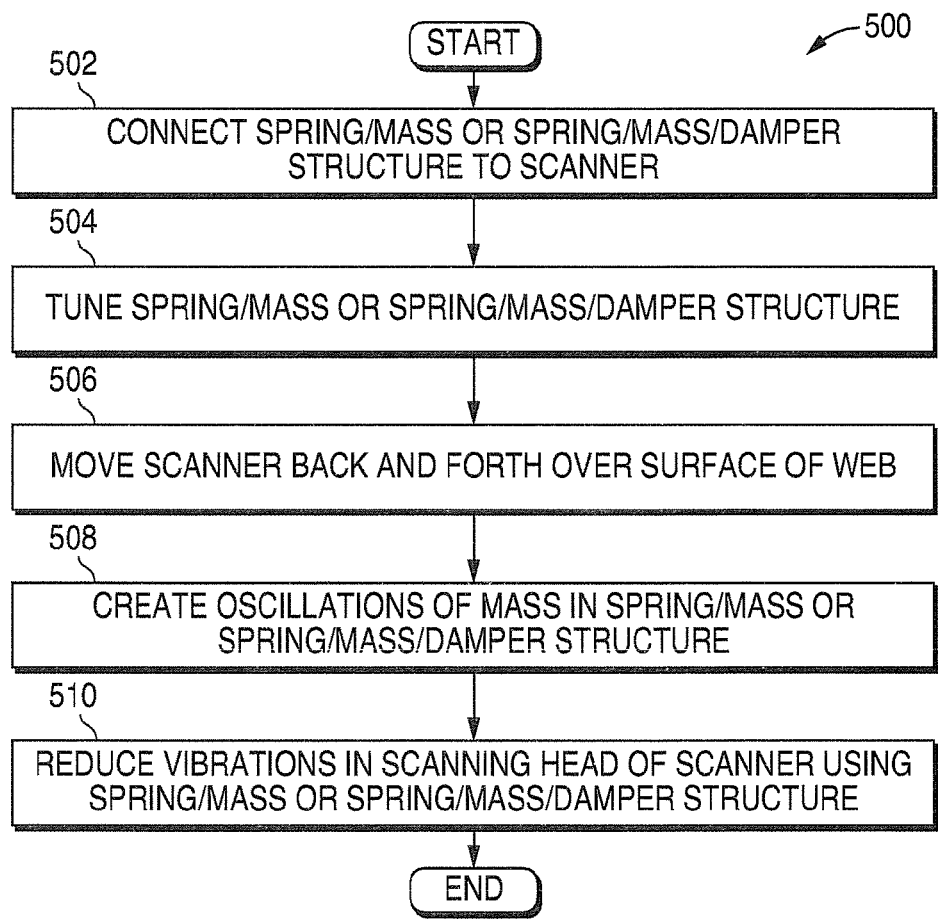
FIG. 5 illustrates an example method for reducing vibrations of scanning sensors in a web manufacturing or processing system according to this disclosure.

FIG. 5 illustrates an example method 500 for reducing vibrations of scanning sensors in a web manufacturing or processing system according to this disclosure. As shown in FIG. 5, a spring/mass or spring/mass/damper structure is connected to a scanner at step 502. This could include, for example, physically connecting the springs 308a-308b to the housing 302 of the scanner 200. This could also include attaching a damper 312 to the mass 306 and the housing 302. This could further include attaching the mass 408 to the web deflector 406, where a portion of the web deflector 406 acts as a spring 410.

The spring/mass or spring/mass/damper structure is tuned for use with the scanner at step 504. This could include, for example, adding one or more plates 307b to or removing one or more plates 307b from the base 307a of the mass 306. A similar mechanism could be used to adjust the mass 408. This could also include selecting a size for the portion of the web deflector 406 acting as the spring 410. As noted above, the physical behavior of a spring/mass or spring/mass/damper structure is well understood. The structure is typically tuned by adjusting the mass 306, 408 and/or springs 308a-308b, 410 based on, among other things, the expected vibration of the scanning head(s) 210-212 without the spring/mass or spring/mass/damper structure and the mass of the scanning head(s) 210-212.

Once tuned, the scanner is placed into operation, and the scanner is moved back and forth over the surface of a web at step 506. This could include, for example, moving the scanning heads 210-212 over the surface of the web 108 so that sensors 216 in the scanning head(s) 210-212 can capture sensor measurements of the web 108. As the scanner is moved, oscillations are created in the spring/mass or spring/mass/damper structure at step 508. This could include, for example, the mass 306, 408 moving back and forth as the scanning head 210 or 212 is moved. The counter-oscillating movement of the mass helps to reduce vibrations in the scanning head(s) of the scanner at step 510.

Although FIG. 5 illustrates one example of a method 500 for reducing vibrations of scanning sensors in a web manufacturing or processing system, various changes may be made to FIG. 5. For example, while shown as a series of steps, various steps in FIG. 5 may overlap, occur in parallel, occur in a different order, or occur multiple times. As a particular example, steps 506-510 could all occur at the same time.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
    a scanning head configured to move one or more sensors back and forth across a surface of a moving web of material;
    a web deflector connected to the scanning head and configured to deflect the web; and
    a vibration dampening device configured to reduce vibrations of the one or more sensors when the scanning head moves the one or more sensors back and forth across the surface of the web, the vibration dampening device comprising at least one mass mounted on a portion of the web deflector, the portion of the web deflector configured to create oscillatory movement of the at least one mass.

2. The apparatus of claim 1, wherein:
    the scanning head comprises a first scanning head configured to move the one or more sensors back and forth across a first surface of the web; and
    the apparatus further comprises a second scanning head configured to move back and forth across a second surface of the web.

3. The apparatus of claim 1, wherein the portion of the web deflector is separated on three of four sides from a remainder of the web deflector.

4. The apparatus of claim 1, further comprising:
    a scanner carriage comprising a housing and a scanning head mount configured to connect the scanning head to the housing.

5. The apparatus of claim 4, wherein the housing is configured to ride on a rail back and forth to move the scanning head across the surface of the web.

6. The apparatus of claim 1, wherein the vibration dampening device further comprises:
    a damper connected to the at least one mass.

7. The apparatus of claim 6, wherein:
    the at least one mass comprises a base having a first mass and one or more plates having one or more second masses attached to the base, a number of plates configurable to adjust a total mass; and
    the damper comprises a device configured to convert kinetic energy into heat.

8. The apparatus of claim 1, wherein the vibration dampening device is tuned to reduce a specific type of vibration of the one or more sensors.

9. The apparatus of claim 8, wherein the vibration dampening device is configured to reduce at least one of horizontal vibrations and vertical vibrations of the one or more sensors.

10. An apparatus comprising:
    a scanning head configured to move back and forth across a surface of a moving web of material;
    a web deflector connected to the scanning head and configured to deflect the web; and
    a vibration dampening device connected to the web deflector and configured to reduce vibrations of the scanning head, the vibration dampening device comprising at least one mass and one or more springs configured to create oscillatory movement of the at least one mass;
    wherein the at least one mass comprises a base having a first mass and one or more plates having one or more second masses attached to the base, a number of plates configurable to adjust a total mass; and
    wherein the one or more springs comprise a portion of the web deflector.

11. The apparatus of claim 10, wherein the at least one mass and the one or more springs are tuned to reduce a specific type of vibration of the scanning head.

12. The apparatus of claim 10, wherein the scanning head comprises one or more sensors configured to measure at least one characteristic of the web.

13. The system of claim 12, wherein the at least one characteristic of the web comprises at least one of: anisotropy, color, gloss, sheen, haze, and surface features of the web.

14. The apparatus of claim 10, further comprising:
    a second web deflector connected to the scanning head.

15. The apparatus of claim 14, further comprising:
    a second scanning head configured to move back and forth across a second surface of the web; and
    third and fourth web deflectors connected to the second scanning head.

16. The apparatus of claim 15, further comprising:
    at least one additional vibration dampening device connected to one or more of the second, third, and fourth web deflectors.

17. A method comprising:
    moving a scanning head back and forth across a surface of a moving web of material, the scanning head comprising one or more sensors measuring at least one characteristic of the web; and
    reducing vibrations of the one or more sensors when the scanning head moves the one or more sensors back and forth across the surface of the web using a vibration dampening device, the vibration dampening device comprising at least one mass and one or more springs that create oscillatory movement of the at least one mass;
    wherein the at least one mass and the one or more springs are located on or within a web deflector connected to the scanning head.

18. The method of claim 17, wherein the scanning head is connected to a scanner carriage that rides on a rail back and forth to move the scanning head across the surface of the web, the scanner carriage comprising a housing.

19. The method of claim 17, wherein the vibration dampening device further comprises:
    a damper connected to the at least one mass.

20. The method of claim 17, wherein the one or more springs comprise a portion of the web deflector.

* * * * *